US012805925B2

(12) United States Patent

Tseng et al.

(10) Patent No.: US 12,805,925 B2

(45) Date of Patent: Nov. 24, 2026

(54) PERCUTANEOUS CUTTER FOR REMOVING DISEASED HEART VALVE LEAFLETS AND RELATED SYSTEMS AND METHODS

(71) Applicants: The United States Government as represented by the Department of Veterans Affairs, Washington, DC (US); The Regents of the University of California, Oakland, CA (US)

(72) Inventors: Elaine Tseng, San Francisco, CA (US); Liang Ge, San Francisco, CA (US); John Ashley, Danville, CA (US); Raghuveer Basude, Fremont, CA (US); Brenna Lord, San Francisco, CA (US)

(73) Assignees: The United States Government as represented by the Department of Veterans Affairs, Washington, DC (US); The Regents of the University of California, Oakland, CA (US)

( * ) Notice: Subject to any disclaimer, the term of this patent is extended or adjusted under 35 U.S.C. 154(b) by 229 days.

(21) Appl. No.: 18/284,497

(22) PCT Filed: Mar. 31, 2022

(86) PCT No.: PCT/US2022/022947

§ 371 (c)(1),
(2) Date: Sep. 27, 2023

(87) PCT Pub. No.: WO2022/212782

PCT Pub. Date: Oct. 6, 2022

(65) Prior Publication Data

US 2024/0366288 A1 Nov. 7, 2024

Related U.S. Application Data

(60) Provisional application No. 63/168,701, filed on Mar. 31, 2021.

(51) Int. Cl.

| | |
|---|---|
| *A61B 18/14* | (2006.01) |
| *A61B 17/32* | (2006.01) |

(Continued)

(52) U.S. Cl.

CPC .. *A61B 18/1445* (2013.01); *A61B 17/320092* (2013.01); *A61B 18/24* (2013.01);

(Continued)

(58) Field of Classification Search

CPC ........ A61B 18/1445; A61B 17/320092; A61B 18/24; A61B 2017/00243;

(Continued)

(56) References Cited

U.S. PATENT DOCUMENTS

| | | |
|---|---|---|
| 5,584,803 A | 12/1996 | Stevens et al. |
| 6,629,534 B1 | 10/2003 | St Goar et al. |

(Continued)

FOREIGN PATENT DOCUMENTS

| | | |
|---|---|---|
| CN | 119235445 | 1/2025 |
| WO | 2023139576 | 7/2023 |

(Continued)

*Primary Examiner* — Paula J Stice

(74) *Attorney, Agent, or Firm* — Ballard Spahr LLP

(57) ABSTRACT

Devices, systems, and methods for removing or dividing valve leaflets, wherein the devices have an elongate shaft and a cutting tool disposed on or near a distal end of the shaft. Certain embodiments include a cutting tool comprising an expandable structure with a cutting element associated with the expandable structure. Other embodiments have a cutting tool that can extend out of an opening in the elongate shaft. Further implementations have a cutting tool that is a laser fiber, an ultrasound emitting tool, or a radiofrequency emitting tool. Some specific embodiments have a first expandable structure disposed at or near a distal end of the elongate shaft, and a second expandable structure disposed on the elongate shaft proximally of the first (Continued)

expandable structure, the second expandable structure comprising at least one distal projection, wherein the at least one distal projection comprises a cutting tool. Other implementations have a cutting tool comprising first and second jaw arms and first and second blades coupled to the first and second jaw arms, respectively.

21 Claims, 10 Drawing Sheets

(51) Int. Cl.
*A61B 18/24* (2006.01)
*A61B 17/00* (2006.01)
*A61B 18/00* (2006.01)

(52) U.S. Cl.
CPC ............... *A61B 2017/00243* (2013.01); *A61B 2017/00557* (2013.01); *A61B 2017/320093* (2017.08); *A61B 2018/00369* (2013.01); *A61B 2018/00601* (2013.01); *A61B 2018/1455* (2013.01)

(58) Field of Classification Search
CPC ......... A61B 2017/00557; A61B 2017/320093; A61B 2018/00369; A61B 2018/00601; A61B 2018/1455; A61B 17/22012; A61B 2017/00783; A61B 2017/22061; A61B 2017/22098; A61B 17/320016; A61B 2017/22097
See application file for complete search history.

(56) References Cited

U.S. PATENT DOCUMENTS

| | | | | |
|---|---|---|---|---|
| 2004/0260322 | A1* | 12/2004 | Rudko .................. | A61B 18/24<br>606/167 |
| 2006/0173475 | A1 | 8/2006 | Lafontaine et al. | |
| 2009/0209955 | A1 | 8/2009 | Forster et al. | |
| 2011/0301699 | A1 | 12/2011 | Saadat | |
| 2015/0216552 | A1* | 8/2015 | Hefer ................. | A61M 25/104<br>606/159 |
| 2016/0135828 | A1 | 5/2016 | Hawkins et al. | |
| 2020/0323545 | A1 | 10/2020 | Or | |
| 2021/0085456 | A1 | 3/2021 | Skarsgard | |
| 2021/0346045 | A1 | 11/2021 | Abunassar | |
| 2023/0301784 | A1 | 9/2023 | Walters et al. | |
| 2024/0398472 | A1 | 12/2024 | Genovese et al. | |
| 2025/0032249 | A1 | 1/2025 | Primeaux et al. | |

FOREIGN PATENT DOCUMENTS

| | | |
|---|---|---|
| WO | 2024157136 | 8/2024 |
| WO | 2025101895 | 5/2025 |

* cited by examiner

PERCUTANEOUS CUTTER FOR REMOVING DISEASED HEART VALVE LEAFLETS AND RELATED SYSTEMS AND METHODS

CROSS-REFERENCE TO RELATED APPLICATION(S)

This application is a national phase filing under 35 U.S.C. § 371 of International Application No. PCT/US2022/022947, filed March 31. 2022, which claims priority the benefit under 35 U.S.C. § 119 (e) to U.S. Provisional Application No. 63/168,701, filed Mar. 31, 2021 and entitled "Percutaneous Cutter for Removing Diseased Heart Valve Leaflets," which are hereby incorporated herein by references in their entireties.

FIELD

The various embodiments herein relate to heart valve treatment devices and procedures, and more specifically to heart valve replacement and/or repair devices and procedures.

BACKGROUND

Heart valves are susceptible to various conditions that can negatively affect their proper functions. These conditions include, but are not limited to, stenosis, regurgitation, infections, and valve disease, including degenerative, myxomatous, and/or fibrotic/calcific valve disease. Stenosis occurs when the leaflets of a valve thicken, stiffen or fuse together. As a result, the valve cannot fully open. The heart then has to work harder to pump blood through the valve, and the body may suffer from a reduced supply of oxygen. The stenosis can be caused by the build-up of calcification or fibrosis. It can also be caused by congenital defects, such as in the case of a bicuspid aortic valve in which two heart valve leaflets are present instead of three, with cusps that are partially or totally fused together (instead of separate). Heart valve infections include, but are not limited to, infective endocarditis or rheumatic fever. These infections lead to poor valve function. Again the heart has to work harder to pump blood, and the body may suffer from a reduction in oxygen. With degenerative or myxomatous valve disease (primarily in the tricuspid or mitral position), the heart valve leaflets slowly degenerate over time, which can lead to prolapse and regurgitation, which again in turn leads to increased workload and stress on the heart and body.

To reduce the increased work the heart is required to perform and restore proper oxygen supply to the body due to these heart valve conditions, it is often desired to either repair a valve (such as a mitral, tricuspid, or occasionally an aortic valve) or implant a new valve to replace the ineffective native valve. In addition to this need to repair or replace the ineffective native heart valve, over time the repaired or replacement valve can also degenerate and need replacement. Increasingly, these valve repairs or replacements are being performed percutaneously by delivering the repair device or replacement valve through a catheter in a collapsed configuration to the heart. Then the repair devices can be deployed or the replacement valves can be expanded inside of the ineffective valve. The replacement valve pushes the leaflets of the ineffective valve open and keeps the diseased valve open by virtue of the expanded stent frame pressed against the valve annulus. However, this opening and crushing of the ineffective valve leaflets limits the size of the replacement valve that can be used inside of the ineffective valve. Although the replacement valve can result in improved valve function and increased blood flow to the body compared to the ineffective valve, the remaining crushed leaflets of the ineffective valve prevent a larger replacement valve from being implanted that could provide even more blood flow to the body. It can be appreciated that each time a replacement valve is delivered inside either a native valve or a replacement valve, the overall size of the implanted replacement valve is less than the previous overall size. At some point, there is not enough room inside a degenerated replacement valve for another replacement valve to function effectively. In such cases, existing ineffective degenerated leaflets are a hindrance to adequate replacement valve hemodynamics. Similarly, in the case of percutaneous valve repair or replacement devices in the mitral or tricuspid position, failure of repair devices or the presence of the myxomatous or degenerated valve leaflets can also impair the ability to place percutaneous valve replacement devices. In the case of failed mitral valve repair devices that grasp leaflets together and create 2 openings, those devices obstruct the ability to place a percutaneous replacement device, some of which have one instead of 2 orifices. For large redundant leaflets in the mitral or tricuspid position when percutaneous mitral or tricuspid replacement valves are needed, those leaflets can obstruct the ventricular outflow tract and reduce functioning of the new percutaneous valve replacement. In any of these scenarios, presence of the prior native, diseased, or replacement leaflets act as a hindrance to new valve function.

There is a need in the art for improved methods and devices for removing or dividing/splitting the leaflets of an ineffective valve.

BRIEF SUMMARY

Discussed herein are various valve leaflet cutting devices and related systems and methods. Each of the devices has an elongate shaft with a cutting tool at or near a distal end of the shaft. Various embodiments have a cutting tool with a sharp edge or blade, while other implementations have an energy emitting cutting tool. Certain embodiments include at least one expandable structure for positioning of the device.

In Example 1, a valve leaflet cutting device comprises an elongate shaft, at least one lumen defined through the elongate shaft, an expandable positioning structure disposed at or near a distal end of the elongate shaft, and a cutting tool operably coupled to the elongate shaft, the cutting tool comprising first and second jaw arms and first and second blades coupled to the first and second jaw arms, respectively.

Example 2 relates to the valve leaflet cutting device according to Example 1, further comprising a cover sheath moveably positionable over the elongate shaft, the cover sheath comprising a centering structure operably coupled to the cover sheath, wherein the centering structure is moveable between a retracted configuration and a deployed configuration.

Example 3 relates to the valve leaflet cutting device according to Example 2, wherein the centering structure comprises an expandable stent-like structure.

Example 4 relates to the valve leaflet cutting device according to Example 1, wherein the expandable positioning structure comprises an expandable balloon attached to the distal end of the elongate shaft.

Example 5 relates to the valve leaflet cutting device according to Example 1, wherein a proximal end of the cutting tool is operably coupled to an external portion of the elongate shaft proximal to a distal end of the elongate shaft.

Example 6 relates to the valve leaflet cutting device according to Example 1, wherein the cutting tool is movable into a closed configuration when an external sheath is urged distally over a proximal end of the cutting tool.

Example 7 relates to the valve leaflet cutting device according to Example 1, wherein the first blade is positionable on a first side of a target leaflet and the second blade is positionable on a second side of the target leaflet.

In Example 8, a valve leaflet cutting device comprises an elongate shaft, at least one lumen defined through the elongate shaft, a first expandable structure disposed at or near a distal end of the elongate shaft, and a second expandable structure disposed on the elongate shaft proximally of the first expandable structure, the second expandable structure comprising at least one distal projection, wherein the at least one distal projection comprises a cutting tool.

Example 9 relates to the valve leaflet cutting device according to Example 8, wherein the first expandable structure comprises an expandable distal balloon, and wherein the second expandable structure comprises an expandable proximal balloon, wherein the at least one distal projection defines a distal opening, wherein the expandable distal balloon is positionable within the distal opening.

Example 10 relates to the valve leaflet cutting device according to Example 9, wherein the at least one distal projection is positionable on a side of a target leaflet opposite the expandable distal balloon.

Example 11 relates to the valve leaflet cutting device according to Example 9, wherein at least one of the expandable distal balloon and the expandable proximal balloon comprises a cutting tool disposed adjacent to a target leaflet.

Example 12 relates to the valve leaflet cutting device according to Example 8, wherein the second expandable structure comprises at least one expandable arm moveably coupled at a proximal end to the elongate shaft.

Example 13 relates to the valve leaflet cutting device according to Example 12, wherein the at least one expandable arm comprises a cutting tool attached at a distal end of the at least one expandable arm, wherein the cutting tool is positionable adjacent to a target leaflet.

Example 14 relates to the valve leaflet cutting device according to Example 12, wherein the at least one expandable arm comprises a support body attached at a distal end of the at least one expandable arm, wherein the support body is positionable adjacent to a target leaflet and on a side of the target leaflet opposite the first expandable structure.

Example 15 relates to the valve leaflet cutting device according to Example 12, wherein the first expandable structure comprises an expandable balloon or an expandable stent-like structure.

In Example 16, a valve leaflet cutting device comprises an elongate shaft, and at least one cutting component associated with the elongate shaft, wherein the at least one cutting component comprises an energy emitting component.

Example 17 relates to the valve leaflet cutting device according to Example 16, wherein the energy emitting component comprises radiofrequency current emitting component, a laser light emitting component, or an ultrasound energy emitting component.

Example 18 relates to the valve leaflet cutting device according to Example 16, wherein the energy emitting component is a structure disposed at a distal end of the elongate shaft, wherein the structure comprises an electrical conducting material and an insulating material, wherein the insulating material is disposed over a portion of the electrical conducting material such that a portion of the electrical conducting material is an exposed conductor.

Example 19 relates to the valve leaflet cutting device according to Example 18, wherein the energy emitting component comprises a loop-shaped structure, wherein the exposed conductor is an energy delivery structure.

Example 20 relates to the valve leaflet cutting device according to Example 16, wherein the elongate shaft comprises at least one lumen, wherein an elongate conductor is disposed through the at least one lumen and operably coupled to the energy emitting component.

In Example 21, valve leaflet cutting device comprises an elongate shaft, at least one lumen defined through the elongate shaft, at least one expandable body disposed at or near a distal end of the elongate shaft, and at least one cutting component associated with the at least one expandable body.

Example 22 relates to the valve leaflet cutting device according to Example 21, wherein the at least one cutting component comprises at least one sharp cutting edge.

Example 23 relates to the valve leaflet cutting device according to Example 21, wherein the at least one cutting component comprises an energy emitting component.

Example 24 relates to the valve leaflet cutting device according to Example 23, wherein the energy emitting component comprises a laser light emitting component or a radiofrequency current emitting component.

Example 25 relates to the valve leaflet cutting device according to Example 23, wherein the at least one cutting component comprises a laser fiber.

Example 26 relates to the valve leaflet cutting device according to Example 21, wherein the at least one cutting component is disposed around an outer surface of the at least one expandable body.

Example 27 relates to the valve leaflet cutting device according to Example 21, wherein the at least one cutting component is disposed through one of the at least one lumens such that the at least one cutting structure is deployable out of an opening defined in the elongate shaft within or adjacent to the at least one expandable body.

Example 28 relates to the valve leaflet cutting device according to Example 21, wherein the at least one cutting component is disposed around an outer circumference of the at least one expandable body.

Example 29 relates to the valve leaflet cutting device according to Example 28, wherein the at least one cutting component is disposed around the outer circumference of the at least one expandable body in a helical configuration.

In Example 30, a valve leaflet cutting device comprises an elongate shaft, at least one lumen defined through the elongate shaft, and at least one cutting component disposable through the at least one lumen, wherein the at least one cutting component comprises an energy emitting component.

Example 31 relates to the valve leaflet cutting device according to Example 30, wherein the energy emitting component comprises a laser light emitting component or a radiofrequency current emitting component.

Example 32 relates to the valve leaflet cutting device according to Example 30, wherein the energy emitting component comprises a laser light fiber disposed through a lumen in the elongate shaft.

Example 33 relates to the valve leaflet cutting device according to Example 32, wherein the elongate shaft comprises an opening defined in a side of the elongate shaft, wherein the opening is in fluidic communication with the lumen.

Example 34 relates to the valve leaflet cutting device according to Example 33, wherein the laser light fiber is extendable out of the opening.

In Example 35, a valve leaflet cutting device comprises an elongate shaft, and at least one cutting component associated with the elongate shaft, wherein the at least one cutting component comprises a radiofrequency current emitting component.

Example 36 relates to the valve leaflet cutting device according to Example 35, wherein the radiofrequency current emitting component is a structure disposed at a distal end of the elongate shaft, wherein the structure comprises an electrical conducting material and a insulating material, wherein the insulating material is disposed over a portion of the electrical conducting material such that a portion of the electrical conducting material is an exposed conductor.

In Example 37, a valve leaflet cutting device comprises an elongate shaft, at least one lumen defined through the elongate shaft, at least one expandable structure disposed at or near a distal end of the elongate shaft, and first and second deployable cutting tools coupled to the elongate shaft. Each of the first and second cutting tools comprises an expandable arm moveably coupled at a proximal end to the elongate shaft, and a cutting device operably coupled to a distal end of the expandable arm, wherein the first and second deployable cutting tools are movable between a retracted position and an expanded configuration.

Example 38 relates to the valve leaflet cutting device according to Example 37, wherein the first and second deployable cutting tools are in a tensioned state when disposed in the retracted position.

Example 39 relates to the valve leaflet cutting device according to Example 37, wherein the at least one expandable structure is a expandable stent structure.

In Example 40, a valve leaflet cutting device comprises an elongate shaft, at least one lumen defined through the elongate shaft, a first expandable structure disposed at or near a distal end of the elongate shaft, and a second expandable structure disposed on the elongate shaft proximally of the first expandable structure, the second expandable structure comprising first and second distal projections, wherein each of the first and second distal projections comprises a cutting tool.

While multiple embodiments are disclosed, still other embodiments will become apparent to those skilled in the art from the following detailed description, which shows and describes illustrative embodiments. As will be realized, the various implementations are capable of modifications in various obvious aspects, all without departing from the spirit and scope thereof. Accordingly, the drawings and detailed description are to be regarded as illustrative in nature and not restrictive.

DETAILED DESCRIPTION

Figure 1A:
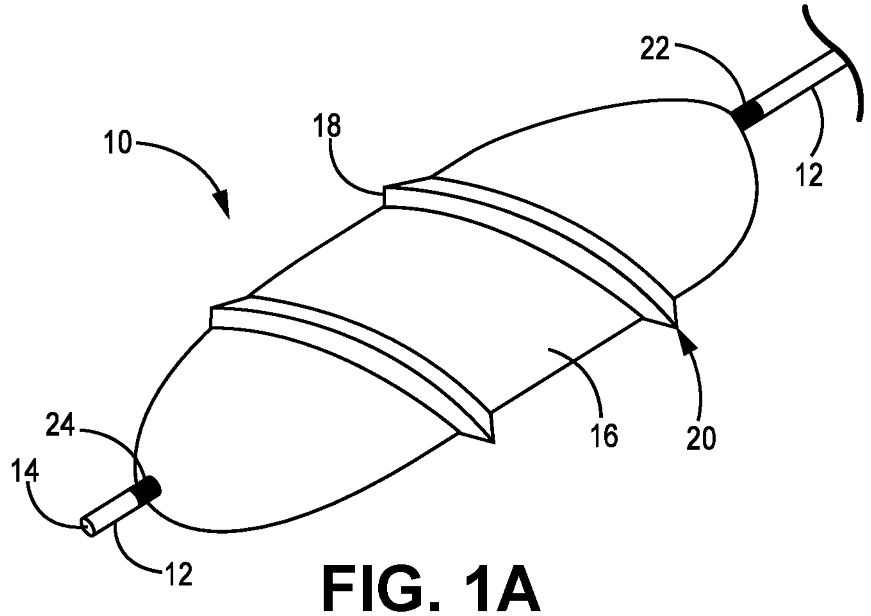
FIG. 1A shows a perspective view of an embodiment of a device for removing heart valve leaflets, according to one embodiment.

Percutaneous devices, systems, and methods are disclosed for cutting and, in certain embodiments, removing valve leaflets within the heart to provide a better substrate for placing a new percutaneous valve. That is, the various implementations herein are configured to remove or split/divide the leaflets of the ineffective valve before a new replacement valve is implanted. The leaflets targeted for removal or division can be native, replacement, or modified leaflets. The leaflet removal eliminates the need for the leaflets to be opened and crushed out of the way by the replacement valve. Thus, the various leaflet cutting and removal device embodiments herein allow for subsequent delivery of a larger replacement valve or prevent the diseased leaflets from obstructing the function of the new valve and, as a result, allow more blood flow to be restored to the body.

As discussed in detail below, the various device embodiments disclosed or contemplated herein include either mechanical actuators or energy delivery to either (1) cut or otherwise separate the valve leaflet from the native annulus or the replacement valve base or (2) split or otherwise divide the valve leaflets at desired locations. The device can also include mechanisms for directing the valve separating mechanism towards the leaflet attachment locations. The system can include guide wire(s), delivery sheath(s) and catheter(s), balloon(s), retrieval device(s), snare(s), grasper(s), and the like. The delivery sheath(s) and catheter(s) can be pre-shaped or steerable to assist proper placement of the valve leaflet cutting devices.

Other technical features may be readily apparent to one skilled in the art from the following figures, descriptions, and claims.

The concept of splitting or dividing one or more leaflets is understood by one of skill in the art to relate to the known method of forming an opening or a split in a leaflet. Exemplary procedures for accomplishing this method include the Basilica and the Lampoon procedures. Various device implementations herein are configured to readily split or divide any target leaflet in this fashion.

This application also contains subject matter that may be related to U.S. Published Patent Application 2021/0022894 and U.S. patent application Ser. No. 17/527,840, filed on Nov. 16, 2021. The entire disclosures of each of the aforementioned applications are hereby incorporated herein by reference.

Various terms are used to refer to particular system components. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct communication between two or more elements, whether or not those elements are in physical contact with one another. Thus, if a first device couples to a second device, that connection may be through a direct connection or through an indirect connection via other devices and connections. The coupling can occur through two or more elements, whether or not those elements are in physical contact with one another. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. Various aspects of the various embodiments disclosed or contemplated herein may be combined in whole or in part to form new embodiments, as evident to those skilled in the art.

The terminology used herein is for the purpose of describing particular example embodiments only and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Figure 1B:
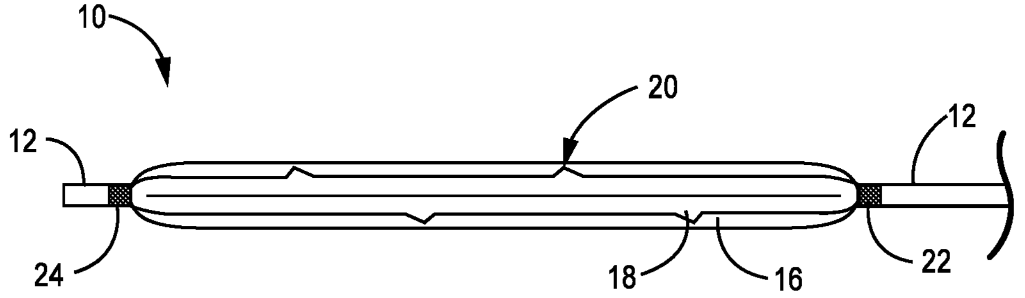
FIG. 1B shows a side view of the embodiment of the device shown in FIG. 1A in a collapsed state for delivery to the heart valve location.
Figure 1C:
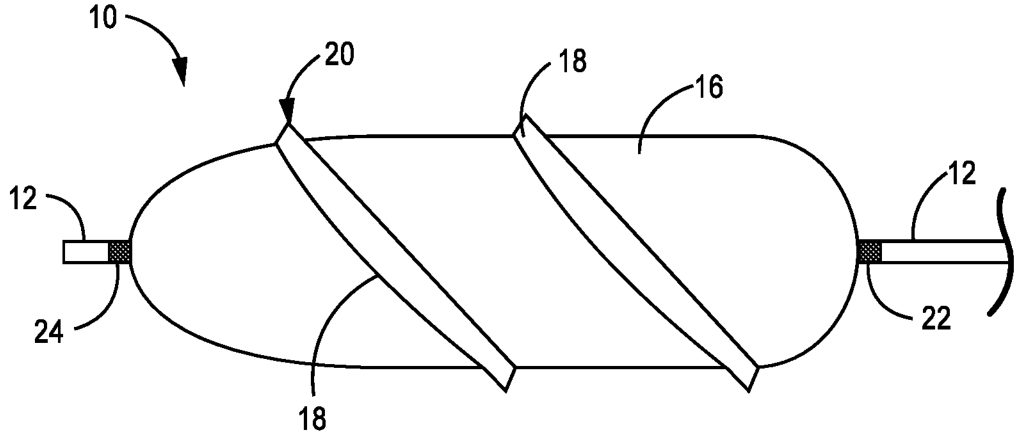
FIG. 1C shows a side view of the embodiment of the device shown in FIG. 1A in an expanded state for removal of heart valve leaflets.

FIGS. 1A-C generally illustrate a heart valve leaflet cutting device 10, according to one embodiment. The leaflet cutting device 10 is comprised of a balloon 16 that is secured to a support shaft 12 at the proximal 22 and distal 24 ends of the balloon 16 and includes one or more cutting elements 18 disposed on its exterior surface. One or more radiopaque markers (not shown) may be placed along the length of the support shaft 12. For example, in one specific implementation, markers (not shown) are disposed at the proximal 22 and distal 24 ends or in other locations to aid in proper placement of the device. These markers may be bands made of a metal or metal and polymer blend which are incorporated into the support shaft 12.

The support shaft 12 may be constructed of a thermoplastic elastomer, such as polyamide, or another polymer or composite of layers of polymer and braided metal. In certain embodiments, the support shaft 12 may include one or more internal lumens 14. In the specific implementation as shown in FIG. 1A, the shaft 12 has one lumen 14. Alternatively, the shaft 12 can have two lumens similar to the lumens 314, 316 depicted in FIGS. 5A-5B and discussed below. Alternatively, the shaft 12 can have three or more lumens. The one or more lumens 14 can be used for passage of a guide wire (not shown) to assist in delivering the leaflet cutting device 10 through the vasculature to the heart valve location. Further, the one or more lumens 14 can be used to deliver fluids such as contrast media to the vasculature. In addition, the one or more lumens 14 can also be used to deliver a fluid to the interior of the balloon 16 to inflate the balloon 16. Any suitable fluid including but not limited to sterile saline can be used to inflate the balloon 16. The balloon 16 may be constructed of nylon, polyethylene terephthalate (PET), or another appropriate material.

The cutting elements 18 include a cutting edge 20 that is configured to cut heart valve leaflets. In one embodiment, the cutting elements 18 can be a single cutting element 18 that is disposed in a spiral configuration around the outer surface of the balloon 16 as shown in FIGS. 1A and 1C. Alternatively, the cutting elements 18 can be more than one structure attached to the outer surface of the balloon 16. These cutting elements 18 are attached to the balloon 16 such that they can expand into a deployed configuration when the balloon 16 is inflated as discussed below. Further, the cutting elements 18 can be constructed of metal, as in a microsurgical blade, a molded polymer, or another suitable material.

The heart valve leaflet cutting device 10 is delivered to the heart valve with the balloon 16 in a deflated configuration as shown in FIG. 1B. In this configuration the cutting edge 20 of the cutting elements 18 are disposed in a retracted position such that the cutting edge 20 does not extend or protrude radially beyond the radial position of the deflated balloon 16. In other words, the retracted cutting edge 20 is disposed within the balloon 16 such that it cannot make physical contact with any external components or tissues. The leaflet cutting device 10 is then inserted into the vasculature over a guide wire and through an introducer sheath. Because of their position, the retracted cutting elements 18 can easily pass through the introducer sheath and through the vasculature without causing any damage to either. The leaflet cutting device 10 is then advanced over the guide wire to the targeted heart valve. The targeted heart valve could be, for example, the aortic valve, the mitral valve, the tricuspid valve or the pulmonary valve. The targeted heart valve could be the native valve, or it could be a replacement tissue valve that was previously implanted either surgically or percutaneously. A delivery catheter can also be used in addition to or instead of the introducer sheath and guide wire to guide the leaflet cutting device 10 to the targeted heart valve.

Once leaflet cutting device 10 is positioned inside the targeted heart valve the balloon 16 is inflated and the cutting elements 18 are pressed against the inside of the valve leaflets. The leaflet cutting device 10 can then be either advanced, rotated, advanced and rotated, retracted, or retracted and rotated relative to the leaflets in order for the cutting edge 20 to separate the leaflets from either the native annulus or from the replacement valve base. The cutting elements 18 and cutting edge 20 can be configured to cut the leaflets with one particular movement of the leaflet cutting device 10. The cutting elements 18 and cutting edge 20 can also be configured to cut leaflets with a combination of movements of the leaflet cutting device 10. After the leaflets have been separated, they can be captured by a retriever or funnel such as that disclosed in U.S. Published Application 2021/0022894 (discussed above) and withdrawn from the body through the vasculature.

Figure 2A:
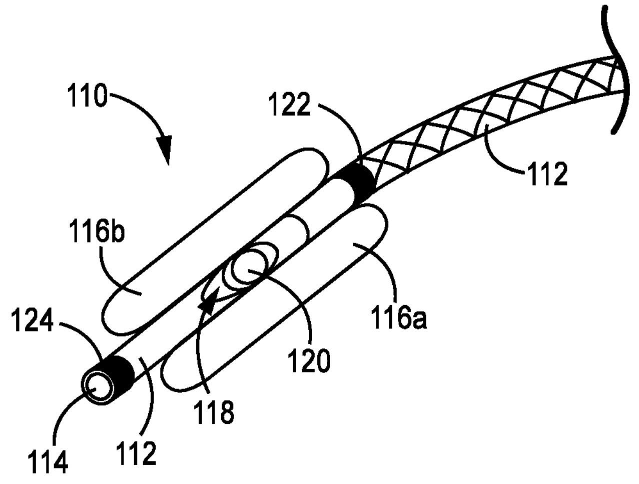
FIG. 2A shows a perspective view of another device for removing heart valve leaflets, according to another embodiment.
Figure 2B:
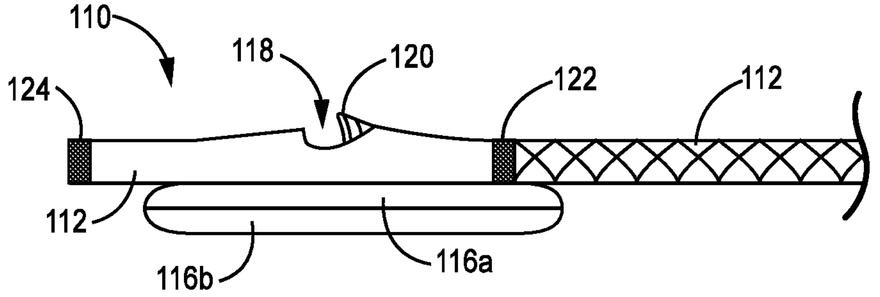
FIG. 2B shows a side view of the embodiment of the device shown in FIG. 2A in a collapsed state for delivery to the heart valve location.
Figure 2C:
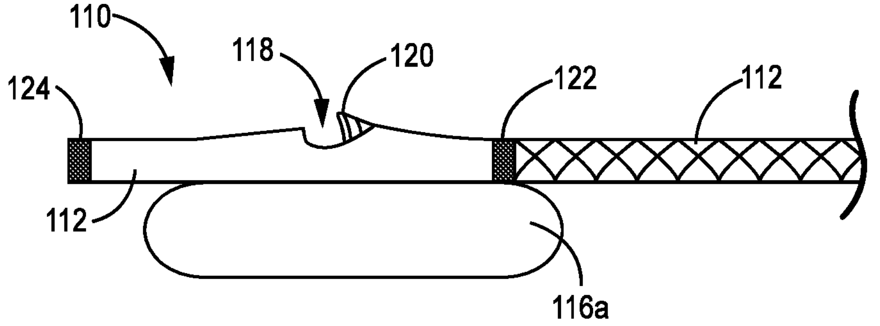
FIG. 2C shows a side view of the embodiment of the device shown in FIG. 2A in an expanded state for removal of heart valve leaflets.

FIGS. 2A-C show an alternate embodiment of a leaflet cutting device 110. The device 110 has certain components and features that are the same or similar to the corresponding components in the device 10 embodiment above, except as discussed herein. The leaflet cutting device 110 is comprised of one or more expansion structures 116*a-b* that are secured to a support shaft 112 at the proximal 122 and distal 124 ends of the structures 116*a-b*. The support shaft 112 includes one or more internal lumens 114. The one or more lumens 114 can be used for passage of a guide wire (not shown) to assist in delivering the leaflet cutting device 110 through the vasculature to the heart valve location. In those implementations in which the expansion structures 116*a*, 116*b* are balloons 116*a*, 116*b*, the one or more lumens 114 can also be used to deliver a fluid to the interior of the balloons 116*a-b* to inflate the balloons 116*a-b*. Further, one lumen 114 is used to receive a cutting tool 120. The support shaft 112 is also comprised of an opening 118 defined in the side of the shaft 112 such that the opening 118 is in fluid communication with the lumen 114. As such, the cutting tool 120 can be urged through the lumen 114 and out of the opening 118 to perform the cutting action necessary to remove the leaflets, as described below.

In one implementation, the cutting tool 120 has an elongate shaft (not shown) with the cutting mechanism at the distal end thereof. In one specific exemplary embodiment, the cutting tool 120 is identical or similar to the cutting tool used in the SilverHawk™ peripheral plaque excision system, which is commercially available from Medtronic, Inc. Alternatively, any known cutting tool that can be positioned through a catheter or sheath can be used.

Figure 7A:
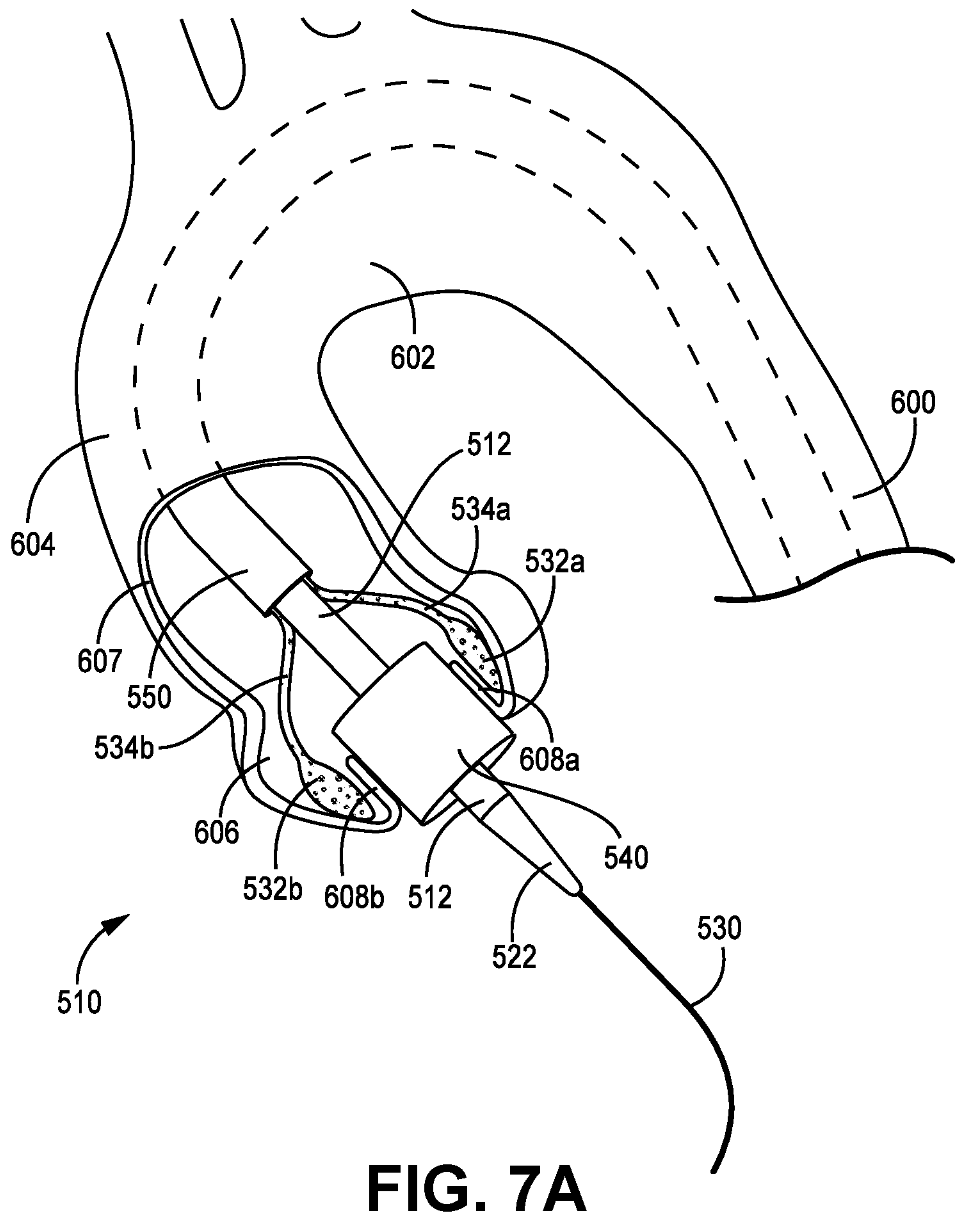
FIG. 7A shows a perspective view of another device for removing heart valve leaflets positioned over the aortic arch and adjacent to a heart valve leaflet location, according to another embodiment.
Figure 7B:
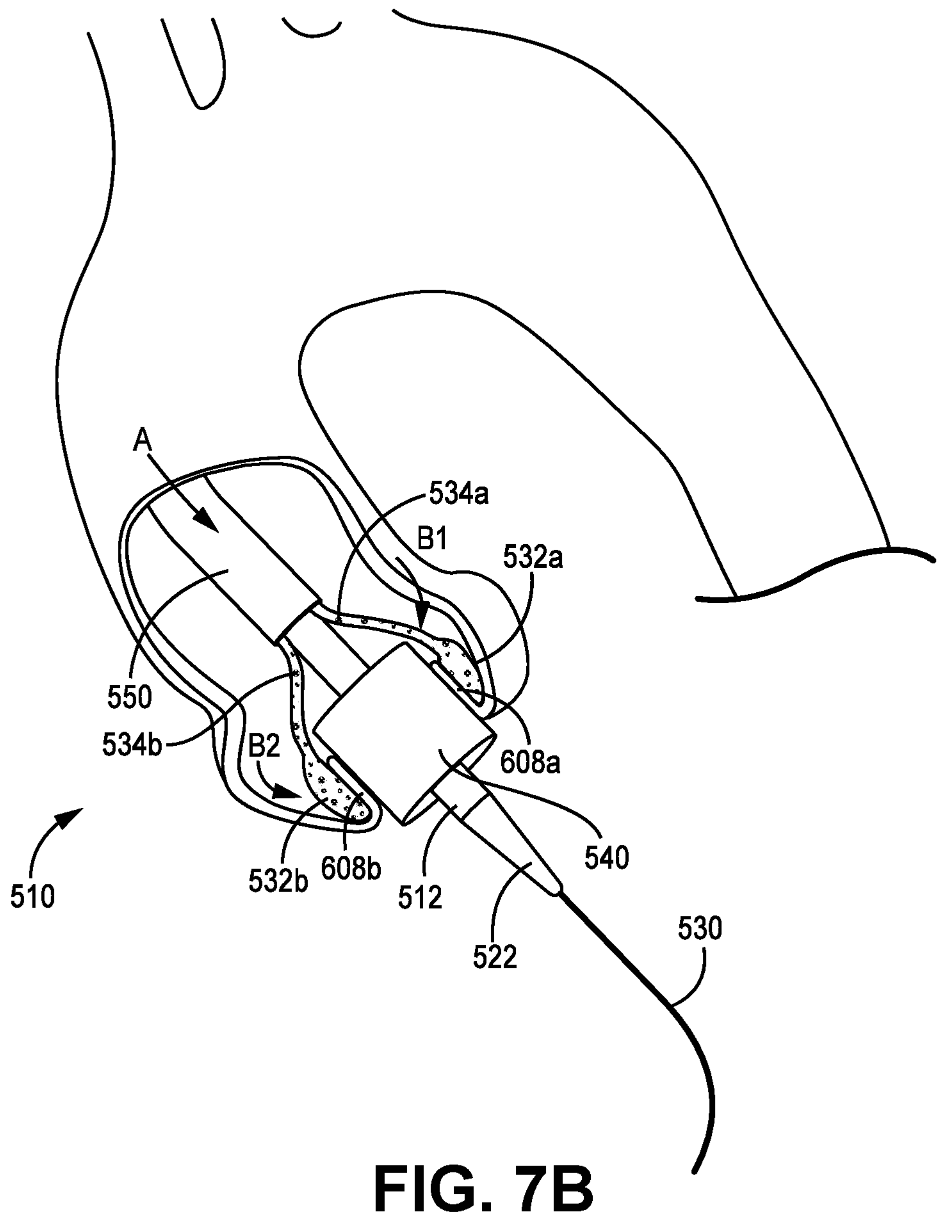
FIG. 7B shows a perspective view of the embodiment of the device shown in FIG. 7A with the device clamping heart valve leaflets.

Further, various alternative embodiments of the cutting device 110 can include at least one opposing force structure disposed on an opposing side of the leaflet to be cut or otherwise removed. More specifically, in one exemplary implementation, the device 110 can have at least one expandable arm similar to the expandable armatures 534*a*, 534*b* discussed below with respect to FIGS. 7A and 7B. Like the armatures 534*a*, 534*b*, the expandable arm can be attached at its proximal end to the support shaft 112 and can extend distally to a position along the length of the device 110 that is substantially radially adjacent to the opening 118 and thus the cutting tool 120. In place of the cutting tool (such as tool 532*a* or 532*b*), at the distal end of the expandable arm is an opposing force body, which can be any structure that has a diameter larger than the arm and can be positioned on the side of the target leaflet opposite the cutting tool 120 as shown in FIGS. 7A and 7B.

In certain embodiments, the expansion structures 116*a*, 116*b* are balloons 116*a*, 116*b*, as discussed above. Alternatively, the one or more expansion structure(s) can be any such known expandable structures, such as expandable frames, stent-like structures or the like. In certain specific implementations, the frames or stent-like structures can be either balloon expandable, self-expanding, or a combination of both balloon expandable and self-expanding.

In a similar manner as was previously described herein, the leaflet cutting device 110 can be inserted through an introducer sheath into the vasculature with the balloons 116*a-b* deflated. Once leaflet cutting device 110 is positioned inside the targeted heart valve, the one or more balloons 116*a-b* are inflated and the cutting tool 120 is extended out of the opening 118 and against the inside of the valve leaflets. The leaflet cutting device 110 can be advanced for the cutting tool 120 to cut the valve leaflet away from the annulus or base or, alternatively, to split or divide the leaflet. The cutting tool 120 can also be attached to a drive shaft (not shown) that is contained in the one or more lumens 114 such that the drive shaft can be rotated and thus the cutting tool 120 is rotated to cut the valve leaflet. In those embodiments having an opposing force structure (not shown) as discussed above, the leaflet is disposed between the cutting tool 120 and the opposing force body such that when the cutting tool 120 is placed into contact with the leaflet to begin cutting the leaflet, the leaflet is urged into contact with and retained in position by the opposing force body, thereby providing the opposing force necessary to allow the cutting tool to cut the leaflet. As was previously described herein, the valve leaflet may be comprised of calcification/fibrosis and be very hard. The cutting tool 120 could be made of a carbide steel that would be significantly harder than the plaque. Rotating the cutting tool 120 with the drive shaft (not shown) can enable separating calcified valve leaflets from the annulus or base or splitting/dividing the leaflets. According to some embodiments, a cut valve leaflet which was separated from the annulus or base can also be guided through the opening 118 into the lumen 114 to capture the cut leaflet and remove it from the body.

Figure 3A:
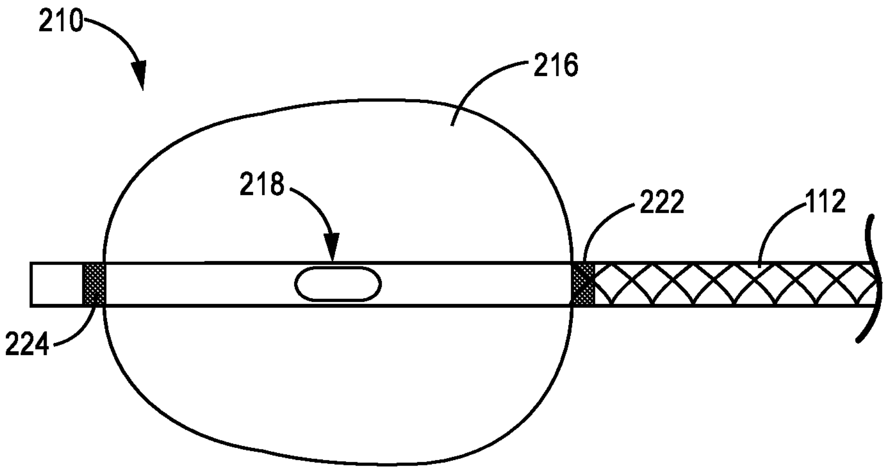
FIG. 3A shows a side view of another device in an expanded state for removing heart valve leaflets according to a further embodiment.
Figure 3B:
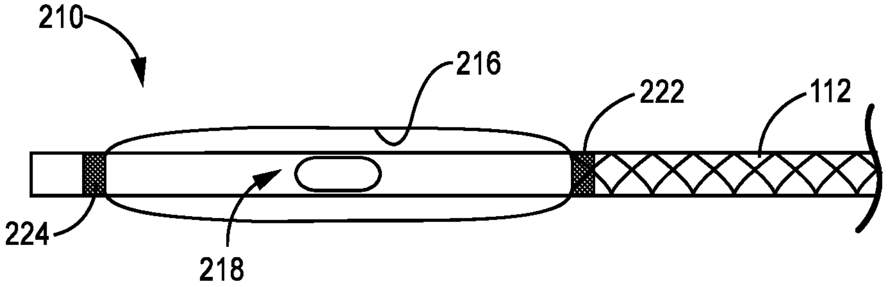
FIG. 3B shows a side view of the embodiment of the device shown in FIG. 3A in a collapsed state for delivery to the heart valve location.
Figure 4:
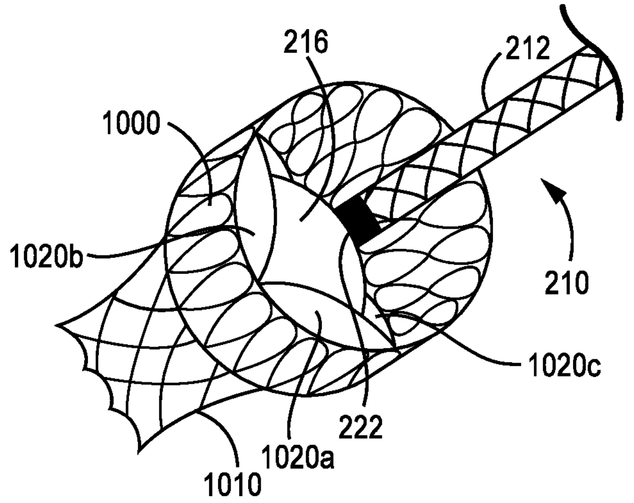
FIG. 4 shows a perspective view of the embodiment of the device shown in FIGS. 3A-B positioned inside a percutaneous replacement heart valve.

The valve leaflet can be split or removed not only by cutting it mechanically as described herein, but also by delivering energy such as laser light or radiofrequency (RF) current to the valve leaflet. FIGS. 3A-B and 4 show an alternate embodiment of a leaflet cutting device 210 that utilizes laser light. The device 210 has certain components and features that are the same or similar to the corresponding components in the device 10, 110 embodiments above, except as discussed herein. The leaflet cutting device 210 is comprised of a balloon 216 that is secured to a support shaft 212 at the proximal 222 and distal 224 ends of the balloon 216. The support shaft 212 includes one or more internal lumens (not shown). The one or more lumens can be used for passage of a guide wire to assist in delivering the leaflet cutting device 210 through the vasculature to the heart valve location. The one or more lumens can also be used to deliver a fluid to the interior of the balloon 216 to inflate the balloon 216. Further, one lumen (not shown) is used to receive a laser fiber (such as the laser fiber 330 discussed below). The support shaft 212 is also comprised of an opening 218 defined in the side of the shaft 212 such that the opening 218 is in fluid communication with the lumen (not shown). As such, the laser fiber (such as fiber 330) can be urged through the lumen and out of the opening 218 to perform the leaflet separation action, as described below. More specifically, the laser fiber can be positioned to direct coherent light from a laser located externally to the body through the support shaft 212 and out the opening 218.

In a similar manner as was previously described herein, the leaflet cutting device 210 can be inserted through an introducer sheath into the vasculature with the balloon 216 deflated as shown in FIG. 3B. Once the leaflet cutting device 110 is positioned inside the targeted heart valve 1000, the balloon 216 is inflated as shown in FIG. 4. Inflating the balloon 216 separates the valve leaflets 1020*a-c* by urging the leaflets 1020*a*-1020*c* into their open positions. The external laser (not shown) can then be activated to deliver energy through the fiber (such as fiber 330) to the valve leaflets 1020*a-c* and thereby separate the valve leaflets from the base 1010. While FIG. 4 shows an example of cutting within a replacement valve, the same mechanisms could be used within a native or modified valve to cut and divide and/or remove heart valve leaflets.

Figure 5A:
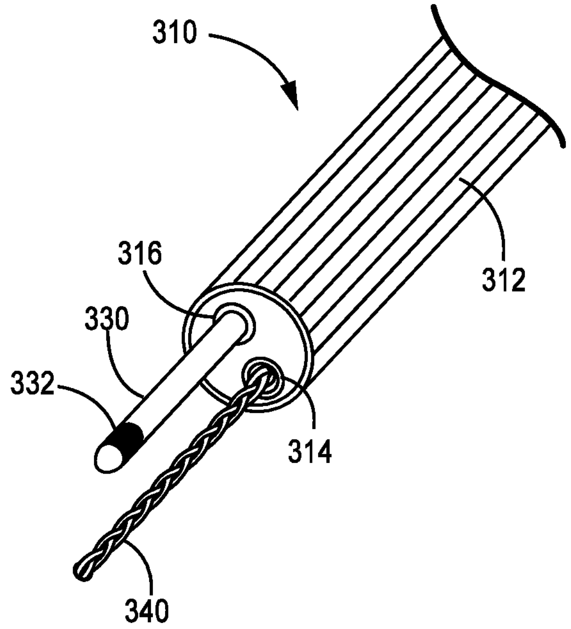
FIG. 5A shows a perspective view of another device for removing heart valve leaflets according to one embodiment.
Figure 5B:
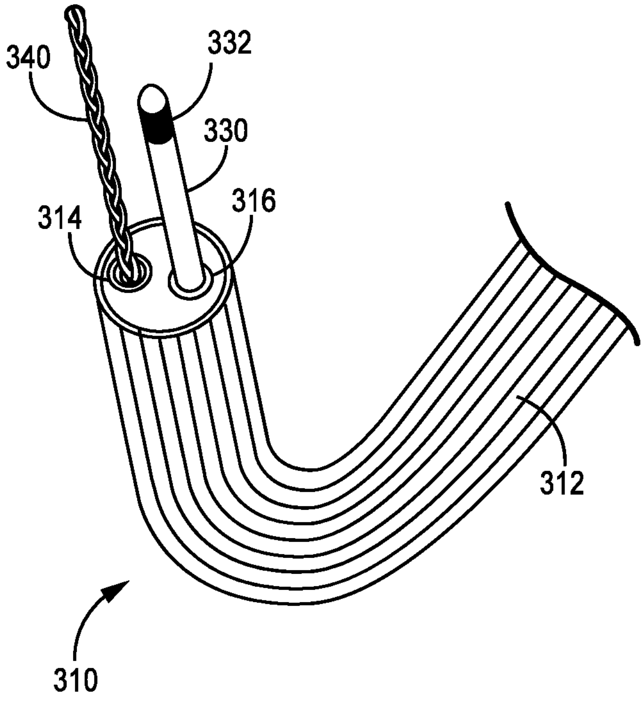
FIG. 5B shows a perspective view of the embodiment of the device shown in FIG. 5A in a deflected state for delivery to the heart valve location.

FIGS. 5A-B illustrate an alternate embodiment of a leaflet cutting device 310 comprised of a laser fiber 330. The device 310 has certain components and features that are the same or similar to the corresponding components in the device 10, 110, 210 embodiments above, except as discussed herein. The leaflet cutting device 310 is also comprised of a support shaft 312 and the support shaft 312 includes internal lumens 314 and internal lumen 316. Lumen 314 is configured for a guide wire 340 that extends through the lumen 314 and guides the leaflet cutting device 330 to the targeted heart valve. Lumen 316 is configured for a laser fiber 330 that can be advanced through the lumen and out the distal end of the support shaft 312. The laser fiber 330 can also be comprised of a marking band 332 that is radiopaque to enable visualization of the location of the distal end of the laser fiber with fluoroscopy. The support shaft 312 can be configured to be steerable or deflectable as is shown in FIG. 5B. By steering or deflecting the support shaft 312, the distal end of the laser fiber 330 can be directed towards the target valve leaflet in order to deliver coherent light to the valve leaflet and thereby separate it from the native annulus or implanted base or, alternatively, split/divide the leaflet and remove it from the body if desired or needed.

In an alternate embodiment, the laser fiber 330 may be encapsulated or otherwise disposed inside an inflatable balloon to enable a blood free zone for both visualization and optimum delivery of the leaflet cutting laser beam.

Figure 6A:
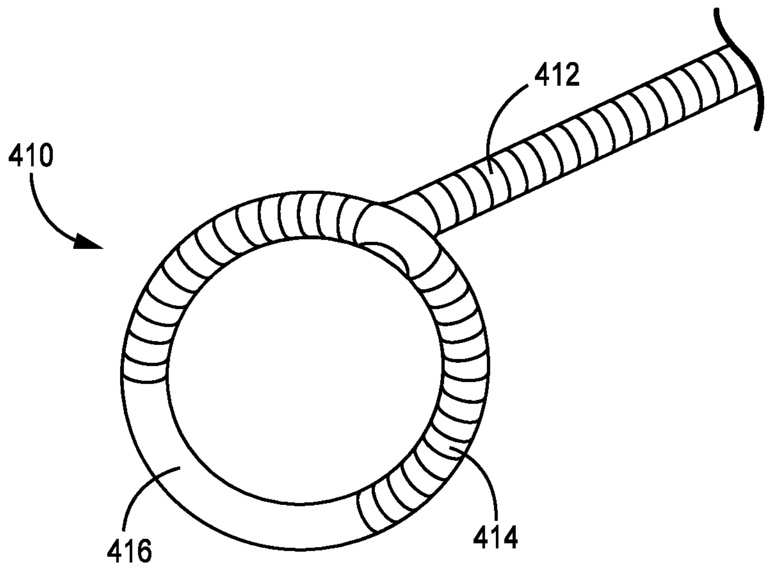
FIG. 6A shows a perspective view of another device for removing heart valve leaflets according to a further embodiment.
Figure 6B:
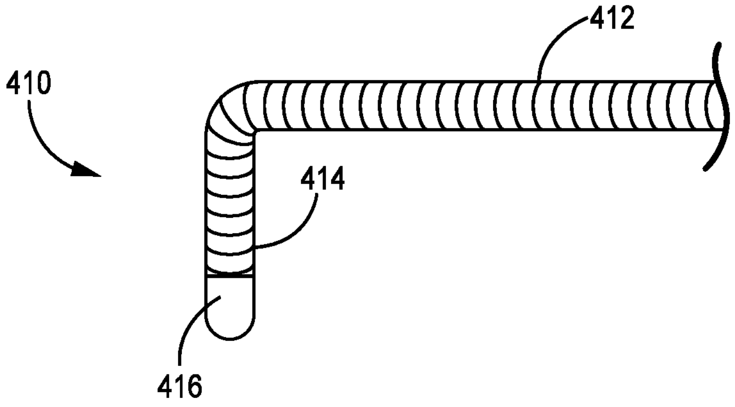
FIG. 6B shows a side view of the embodiment of the device shown in FIG. 6A.

FIGS. 6A-B illustrate a heart valve leaflet cutting device 410 that utilizes radiofrequency current, in accordance with another implementation. The device 410 has certain components and features that are the same or similar to the corresponding components in the device 10, 110, 210, 310 embodiments above, except as discussed herein. The leaflet cutting device 410 is comprised of a shaft 412 and a distal loop 414. The shaft 412 and a portion of the distal loop 414 are covered with an electrically insulating material. Another portion 416 of the distal loop 414 is not insulated—this uninsulated portion 416 is the current delivery component 416. The current delivery component 416 is comprised of an electrical conducting material such as, but not limited to, platinum, gold, or silver. The electrically conducting material can extend proximally inside the insulated shaft 412 to an electrical generator (not shown) located outside of the body. The electrical generator is configured to deliver radiofrequency (RF) current to the current delivery component 416 via the electrically conducting material. This RF current can be delivered to the valve leaflet to separate or cut the valve leaflet from the native annulus or implanted base or split/divide the leaflet. The heart valve cutting device 410 can be delivered through a supporting shaft 12 as was previously described herein.

FIGS. 7A-B illustrate a heart valve leaflet cutting device 510, according to another implementation. The device 510 has certain components and features that are the same or similar to the corresponding components in the device 10, 110, 210, 310, 410 embodiments above, except as discussed herein. As shown, the device 510 has been delivered through the vasculature up the descending aorta 600 over the aortic arch 602 and down the ascending aorta 604 to a location proximate to the targeted valve leaflets 608*a* and 608*b*. In this figure, a portion 607 of ascending aorta 604 is cut away (schematically removed) to show the heart valve leaflet cutting device 510, the targeted leaflets 608*a* and 608*b*, and the pockets behind each valve leaflet (called the sinus of valsalva or aortic sinus 606). The heart valve leaflet cutting device 510 is comprised of a support shaft 512 that is directed over a guide wire 530. The support shaft 512 can include a distal tapered nose 522 to assist in atraumatic advancement of the heart valve leaflet cutting device 510 through the vasculature. The support shaft 512 also delivers a leaflet support cage 540. The leaflet support cage 540 is collapsed for delivery into and through the vasculature. Once positioned inside the targeted valve leaflets 608*a* and 608*b* the leaflet support cage 540 is expanded up against the inside of the targeted valve leaflets 608*a* and 608*b* (as shown in FIG. 7A). The heart valve leaflet cutting device 510 also includes leaflet cutters 532*a* and 532*b* which are collapsed against the support shaft 512 for delivery into and through the vasculature. Once positioned proximal of the targeted valve leaflets 608*a* and 608*b* the leaflet cutters 532*a* and 532*b* are expanded outwardly by withdrawing the cover sheath 550 (as shown in FIG. 7A). The cover sheath 550 continues proximally through the vasculature as shown by the dashed lines. The leaflet cutters 532*a* and 532*b* are attached to the support shaft 512 by expandable armatures 534*a* and 534*b*.

The leaflet cutters 532*a* and 532*b* can be configured in any of the variety of manners previously detailed in the present disclosure including but not limited to microsurgical metal or polymer blade, a rotating cutting edge, a laser, and/or a radiofrequency cutting current. The leaflet cutters 532*a* and 532*b* can also be configured with a transducer to deliver high frequency ultrasound energy for dissecting the targeted leaflets 608*a* and 608*b*. The expandable armatures 534*a* and 534*b* and the leaflet support cage 540 can be made from flexible metallic or polymer materials. The expandable armatures 534*a* and 534*b* can also be made from super elastic material such as nickel titanium alloys commonly known as Nitinol. The guide wire 530 and support shaft 512 can be made of similar types of materials as were previously described in the present disclosure for other guide wires and support shafts. The cover sheath 550 can also be made of similar types of materials as were previously described in the present disclosure for support shafts.

In this implementation, the support structure 540 serves as the opposing force or support positioned on the side of the leaflet opposite the cutting tools 532*a*, 532*b* (in a fashion similar to the support arms providing support in certain embodiments relating to the device 110 described above with respect to FIGS. 2A-2C). In use, as shown in FIGS. 7A and 7B, the leaflets 608*a*, 608*b* are disposed between the cutting tools 532*a*, 532*b* and the opposing force body (in this case, the support cage or structure 540) such that when the cutting tools 532*a*, 532*b* are placed into contact with the leaflets 608*a*, 608*b* to begin cutting the leaflets 608*a*, 608*b*, the leaflets 608*a*, 608*b* are urged into contact with and retained in position by the opposing force body (the support cage or structure) 540, thereby providing the opposing force necessary to allow the cutting tools 532*a*, 532*b* to cut the leaflets 608*a*, 608*b*.

Alternatively, in various embodiments of this device 510, the expandable central structure 540 can be the cutting tool (or have a cutting tool attached thereto) and the bodies 532*a*, 532*b* on the arms 534*a*, 534*b* can be the opposing force bodies 532*a*, 532*b*, in a configuration similar to the alternative configuration described above with respect to the device 110 of FIGS. 2A-2C.

In FIG. 7B, the cover sheath 550 is advanced axially in a distal direction over the support shaft 512 as indicated by Arrow A. The cover sheath 550 advances over the expandable armatures 534*a* and 534*b*, which urges the expandable armatures 534*a* and 534*b* radially towards the support shaft 512 (Arrows B1 and B2). This in turn drives the leaflet cutters 532*a* and 532*b* radially through the valve leaflets 608*a* and 608*b*, thereby separating the leaflets 608*a*, 608*b* from the annulus. The dissected valve leaflets 608*a* and 608*b* are then held against the leaflet support cage 540 as the cover sheath 550 is further advanced, collapsing the leaflet support cage 540 and the dissected valve leaflets 608*a* and 608*b* against the support shaft 512. The entire heart valve leaflet cutting device 510 can then be withdrawn from the vasculature with the dissected and trapped valve leaflets 608*a*, 608*b*.

In this example only two valve leaflets 608*a* and 608*b* and two leaflet cutters 532*a* and 532*b* are shown. However, the entire heart valve leaflet cutting device 510 can be comprised of one, two, three, of four leaflet cutters for dissecting and removing one, two, three, or four native or replacement heart valve leaflets. While this example illustrates removal of aortic valve leaflets, the device can be employed to enable leaflet removal from other heart valves through percutaneous or surgical approaches, such as an apical or transseptal approach to the mitral valve or venous approach to the tricuspid valve. The leaflets targeted for removal or division may be native, replacement (through surgery or TAVR, for example), or modified (such as with a clip placed previously).

In certain alternate embodiments, the leaflet cutters 532*a* and 532*b* may be used to cut prosthetic leaflets of a previously implanted prosthetic valve (rather than natural leaflets). Further, any of the various embodiments herein can be used to remove or divide/split such prosthetic leaflets of a prosthetic valve.

Figure 8:
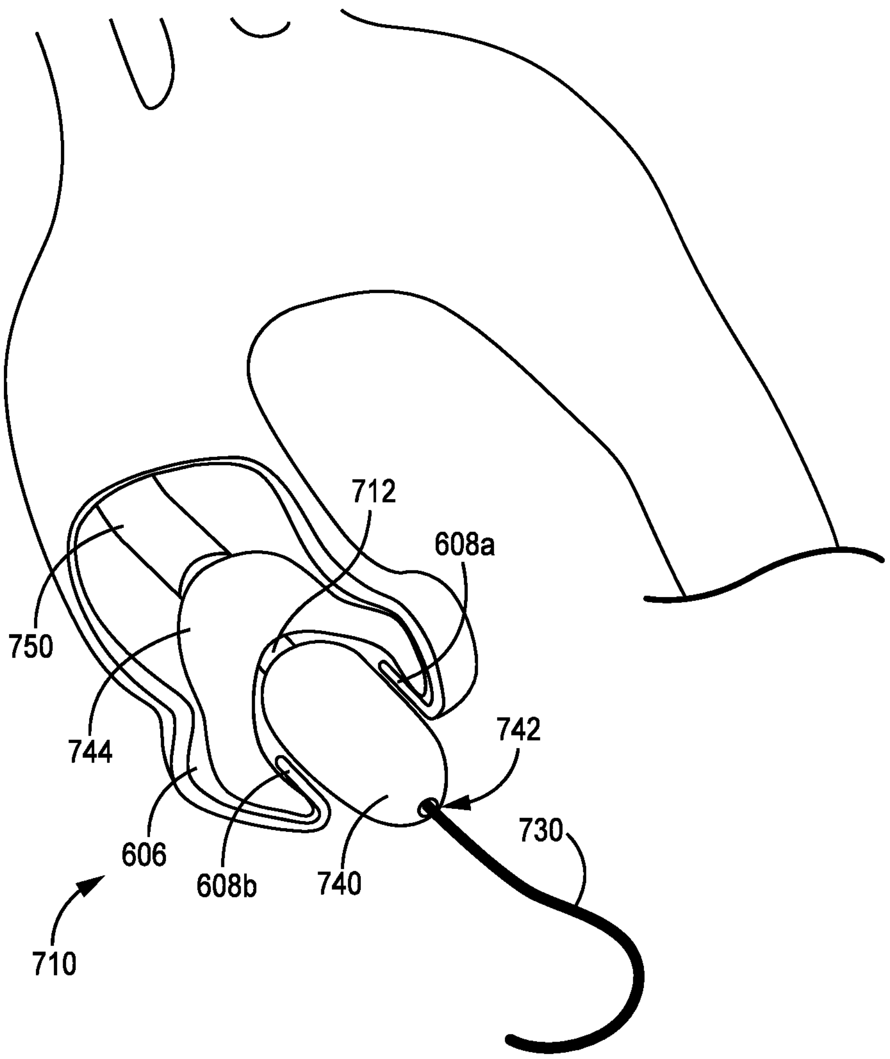
FIG. 8 shows a perspective view of another device for removing heart valve leaflets, according to yet another embodiment.

FIG. 8 illustrates a further embodiment of a heart valve leaflet cutting device 710 that has been delivered through the vasculature to dissect valve leaflets 608*a* and 608*b*. The device 710 has certain components and features that are the same or similar to the corresponding components in the device 10, 110, 210, 310, 410, 510 embodiments above, except as discussed herein. The heart valve leaflet cutting device 710 is advanced over a guide wire 730. The guide wire 730 can be any number of known vascular guide wires with a variety of characteristics including but not limited to a "J" tip as shown in FIG. 8. The heart valve leaflet cutting device 710 includes a central lumen 742 through which the guide wire 730 passes. The heart valve leaflet cutting device 710 also includes a support shaft 712 on which is mounted a central balloon 740. The central balloon is collapsed for advancing the heart valve leaflet cutting device 710 into and through the vasculature. Once the central balloon 740 is positioned inside the valve leaflets 608*a* and 608*b*, the central balloon 740 is expanded as was previously described in the present disclosure. A second sinus balloon 744 is also mounted on the support shaft 712. As with the central balloon 740 the sinus balloon 744 is collapsed for advancing the heart valve leaflet cutting device 710 into and through the vasculature. When expanded, the sinus balloon 744 expands into the sinus of valsalva 606 on the outside of valve leaflets 608*a* and 608*b*. In this manner the central balloon 740 and sinus balloon 744 are configured to sandwich the valve leaflets 608*a* and 608*b* in between. Either or both of the central balloon 740 or the sinus balloon 744 can be cutting balloons (or have cutting tools associated therewith) as was previously described in the present disclosure such that expanding the central balloon 740 or the sinus balloon 744 together results in dissecting the leaflets 608*a* and 608*b*. Thus, one or both of the balloons 740, 744 serve as the opposing force or support positioned on the side of the leaflets 608*a*, 608*b* opposite the cutting balloon(s) (in a fashion similar to the opposing force/support structures described above).

While the sinus balloon 744 as depicted appears to have solely two distal projections, each of which is disposed in the sinus of valsalva 606 as discussed above, in some embodiments, the balloon 744 has a single distal projection that extends around the full circumference of the balloon 744 and defines a unitary opening therein (to receive the central balloon 740) such that the projection encircles all three of the leaflets (including 608*a*, 608*b*, and the third, which is not visible and thus not identified with a reference number). Alternatively, the distal projection of the balloon 744 can be made up of three projections-one for each of the target leaflets. In a further alternative, the sinus balloon 744 can be made up of two or more balloons, each with at least one distal projection.

Once leaflets 608*a* and 608*b* are dissected, the central balloon 740 and sinus balloon 744 can be collapsed and the cover sheath 750 can be advanced to capture the central balloon 740, the sinus balloon 744, and the dissected leaflets 608*a* and 608*b*. The dissected leaflets 608*a* and 608*b* can then be removed from the vasculature along with the heart valve leaflet cutting device 710.

The heart valve leaflet cutting device 710 does not need to have two balloons but rather can be configured with one balloon and one of the expanding devices from heart valve leaflet cutting device 510. For example, the heart valve leaflet cutting device 710 can be comprised of a central balloon 740 and leaflet cutters 532*a* and 532*b*. The leaflet cutters 532*a* and 532*b* can dissect the leaflets 608*a* and 608*b* against the central balloon 740. Alternately the heart valve leaflet cutting device 710 can be comprised of a sinus balloon 744 and a leaflet support cage 540. The sinus balloon 744 can be a cutting balloon that dissects the leaflets 608*a* and 608*b* against the leaflet support cage 540.

Figure 9A:
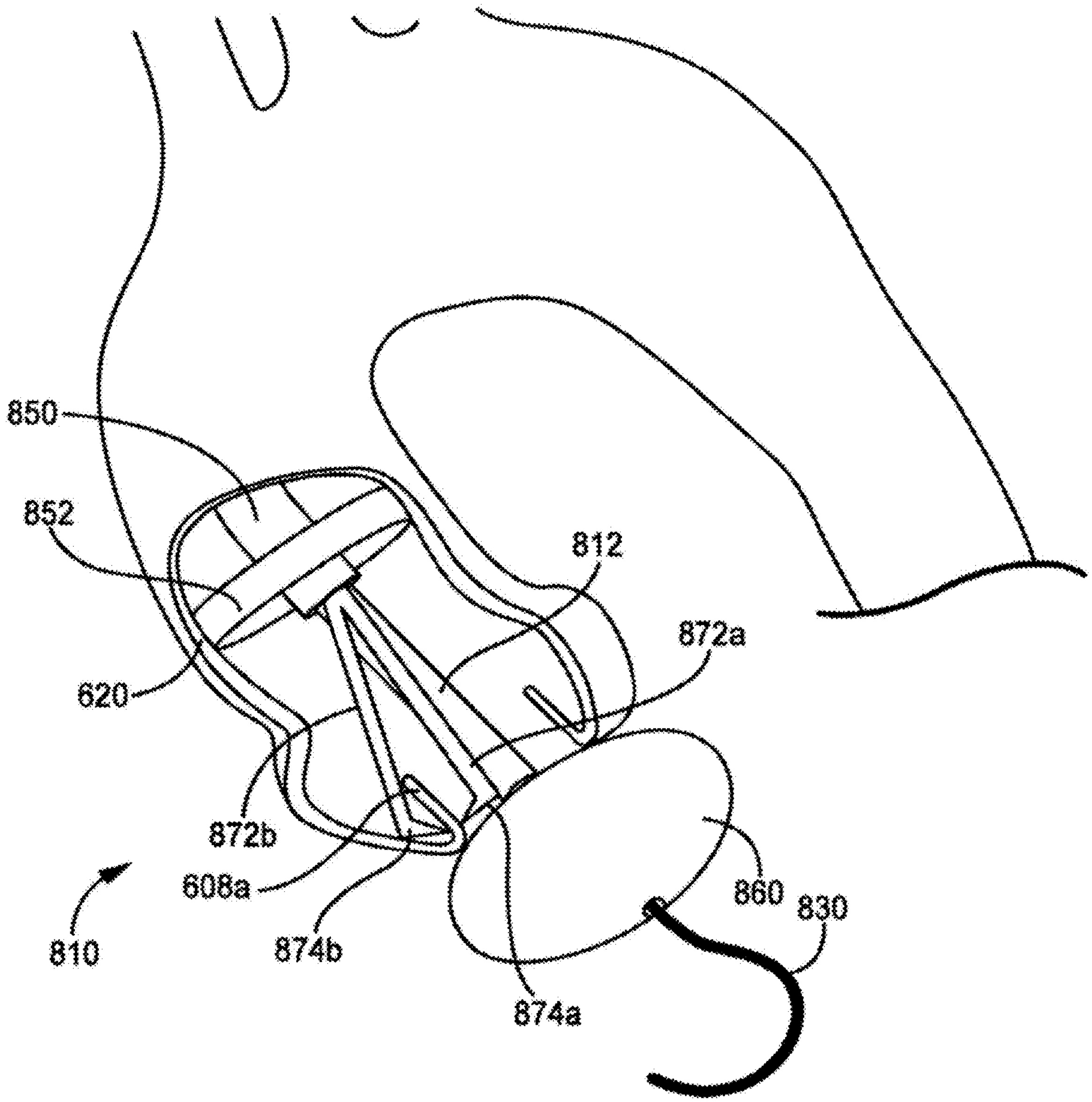
FIG. 9A shows a perspective view of a further device for removing heart valve leaflets, according to an additional embodiment.
Figure 9B:
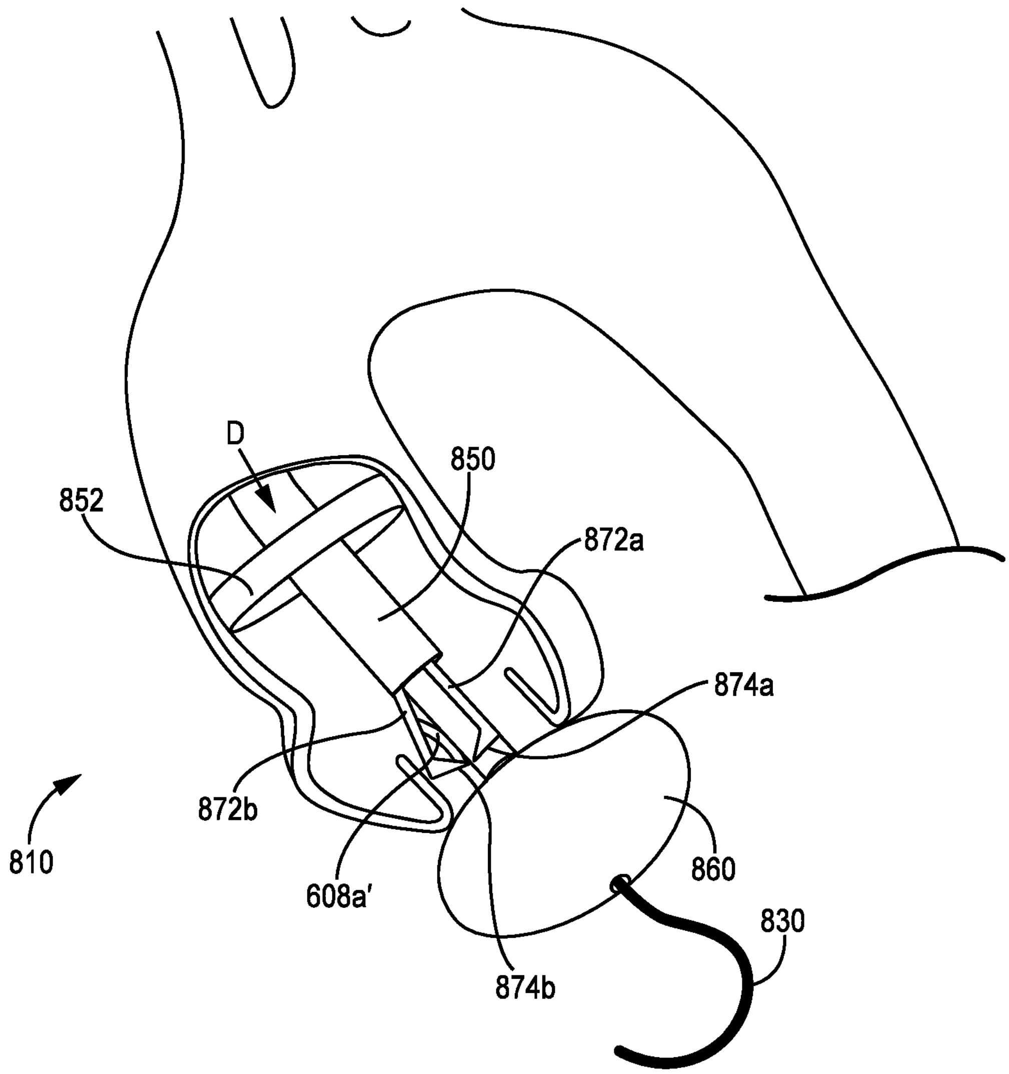
FIG. 9B shows a perspective view of the embodiment of the device shown in FIG. 9A with the device engaging and dissecting out a heart valve leaflet.

FIGS. 9A and 9B illustrate another heart valve leaflet cutting device 810 implementation that can be advanced over a guide wire 830 through the vasculature to a leaflet 608*a*. The device 810 has certain components and features that are the same or similar to the corresponding components in the device 10, 110, 210, 310, 410, 510, 710 embodiments above, except as discussed herein. The heart valve leaflet cutting device 810 is comprised of a support shaft 812 on which is mounted a positioning balloon 860. The positioning balloon 860 is collapsed for advancing the heart valve leaflet cutting device 810 into and through the vasculature. Once the positioning balloon 860 is located distal the valve leaflets 608*a* and 608*b*, the positioning balloon 860 is expanded as was previously described in the present disclosure. The heart valve leaflet cutting device 810 is also comprised of a cover sheath 850 on which is mounted a centering cage 852. The centering cage 852 is collapsed for advancing the heart valve leaflet cutting device 810 into and through the vasculature. Once the centering cage 852 is located proximal of the valve leaflet 608*a*, the centering cage 852 is expanded against the inner diameter of the vasculature to center the cover sheath 850. The cover sheath 850 can be withdrawn to expose leaflet cutting jaws (or "blades") 874*a* and 874*b*. The leaflet cutting jaws 874*a* and 874*b* are configured at the ends of leaflet jaw arms 872*a* and 872*b*. Alternatively, a single blade can be disposed on one of the two arms 872*a*, 872*b* such that it accomplishes the same cutting action when it contacts the other arm. When the cover sheath 850 is withdrawn the leaflet jaw arms 872*a* and 872*b* expand such that the leaflet cutting jaws 874*a* and 874*b* are positioned on the inside and outside of the valve leaflet 608*a*. The leaflet jaw arms 872*a* and 872*b* are biased away from the central axis of the heart valve leaflet cutting device 810 toward the targeted valve leaflet 608*a*.

By advancing the cover sheath 850 distally as shown by Arrow D in FIG. 9B the leaflet jaw arms 872*a* and 872*b* are closed down towards each other such that the leaflet cutting jaws 874*a* and 874*b* dissect the valve leaflet 608*a*. The dissected valve leaflet 608*a*' is captured inside the cover sheath 850 and the centering cage 852 and positioning balloon 860 are collapsed so that the dissected valve leaflet 608*a*' and the entire heart valve leaflet cutting device 810 can be removed from the vasculature.

The dissection of the valve leaflet 608*a* and/or 608*b* as described herein can be in whole or in part. If only part of the valve leaflet 608*a* and/or 608*b* is dissected with one pass of the heart valve leaflet cutting device 510, 710 or 810, the heart valve leaflet cutting device can be reintroduced into the vasculature to dissect additional portions of the valve leaflet 608*a* and/or 608*b* as many times as is required to remove sufficient amounts of the valve leaflet 608*a* and/or 608*b* and/or to remove additional native or replacement valve leaflets, as necessary, including removal of modified leaflets.

In various implementations, any of the device embodiments herein can be used in conjunction with a locating device and/or method that utilizes the patient's own anatomy to assist with directing the cutting device to the targeted area. For example, U.S. Pat. No. 9,044,316, which issued Jun. 2, 2015 and is hereby incorporated herein by reference in its entirety, discloses one such device that could be used with any of the devices herein. Alternatively, any similar known locating device could also be used. Further, in certain embodiments, any of the device implementations herein can be used in conjunction with a capture and removal device for use in the cardiovascular system. One exemplary device and method for removing an obstruction from a patient that can be used with any of the devices herein is described in U.S. Pat. No. 7,727,243, which issued Jun. 1, 2010 and is hereby incorporated herein by reference in its entirety. Alternatively, any similar object capture and removal device can also be used.

Although the various embodiments have been described with reference to preferred implementations, persons skilled in the art will recognize that changes may be made in form and detail without departing from the spirit and scope thereof.

What is claimed is:

1. A valve leaflet cutting device comprising:

(a) an elongate shaft;

(b) at least one lumen defined through the elongate shaft;

(c) a first expandable structure disposed at or near a distal end of the elongate shaft;

(d) a second expandable structure; and (e) a cutting tool operably coupled to the elongate shaft, wherein the cutting tool comprises a blade, wherein the first and second expandable structures are axially movable relative to each other to simultaneously receive a plurality of valve leaflets therebetween, and wherein the cutting tool is configured to cut the plurality of valve leaflets by pressure applied by the blade to the plurality of leaflets while the plurality of valve leaflets are received between the first and second expandable structures.

2. The valve leaflet cutting device of claim 1, further comprising a cover sheath moveably positionable over the elongate shaft, the cover sheath comprising a centering structure operably coupled to the cover sheath, wherein the centering structure is moveable between a retracted configuration and a deployed configuration.

3. The valve leaflet cutting device of claim 2, wherein the centering structure comprises an expandable stent-like structure.

4. The valve leaflet cutting device of claim 1, wherein the first expandable structure comprises an expandable balloon.

5. The valve leaflet cutting device of claim 1, wherein a proximal end of the cutting tool is operably coupled to an external portion of the elongate shaft.

6. The valve leaflet cutting device of claim 1, wherein the first expandable structure comprises an expandable stent-like structure.

7. The valve leaflet cutting device of claim 1, wherein the first and second expandable structures are axially movable relative to each other to permit at least a portion of the first expandable structure to overlap with at least a portion of the second expandable structure along a longitudinal axis.

8. The valve leaflet cutting device of claim 1, wherein the at least a portion of the first expandable structure is receivable within the at least a portion of the second expandable structure.

9. The valve leaflet cutting device of claim 1, wherein the first expandable structure is attached to the distal end of the elongate shaft.

10. The valve leaflet cutting device of claim 1, wherein the cutting tool is associated with the first expandable structure.

11. The valve leaflet cutting device of claim 1, wherein the blade of the cutting device is disposed on the first expandable structure.

12. The valve leaflet cutting device of claim 1, wherein the cutting tool is associated with the second expandable structure.

13. The valve leaflet cutting device of claim 1, wherein the second expandable structure comprises a balloon.

14. The valve leaflet cutting device of claim 1, wherein the second expandable structure comprises a plurality of expandable armatures.

15. A valve leaflet cutting device comprising:

(a) an elongate shaft;

(b) at least one lumen defined through the elongate shaft;

(c) a first expandable structure disposed at or near a distal end of the elongate shaft;

(d) a second expandable structure; and (e) a cutting tool operably coupled to the elongate shaft, wherein the cutting tool comprises a sharp cutting edge, wherein the sharp cutting edge is sufficiently sharp to cut valve leaflet tissue, wherein the first and second expandable structures are axially movable relative to each other to simultaneously receive a plurality of valve leaflets therebetween, and wherein the cutting tool is configured to cut the plurality of valve leaflets by pressure applied by the sharp cutting edge to the plurality of leaflets while the plurality of valve leaflets are received between the first and second expandable structures.

16. The valve leaflet cutting device of claim 15, wherein the first expandable structure comprises an expandable stent-like structure.

17. The valve leaflet cutting device of claim 15, wherein the first and second expandable structures are axially movable relative to each other to permit at least a portion of the first expandable structure to overlap with at least a portion of the second expandable structure along a longitudinal axis.

18. The valve leaflet cutting device of claim 15, wherein the at least a portion of the first expandable structure is receivable within the at least a portion of the second expandable structure.

19. The valve leaflet cutting device of claim 15, wherein the first expandable structure is attached to the distal end of the elongate shaft.

20. The valve leaflet cutting device of claim 15, wherein the cutting tool is associated with the first expandable structure.

21. The valve leaflet cutting device of claim 15, wherein the cutting tool is associated with the second expandable structure.

* * * * *